United States Patent [19]

Geary et al.

[11] Patent Number: 4,950,259
[45] Date of Patent: Aug. 21, 1990

[54] PERITONEAL DIALYSIS CATHETER SUITABLE FOR PERMANENT IMPLANT

[75] Inventors: Denis F. Geary, Willowdale; Andrej Bahoric, Don Mills, both of Canada

[73] Assignee: HSC Research Development Corporation, Toronto, Canada

[21] Appl. No.: 256,456

[22] Filed: Oct. 12, 1988

[30] Foreign Application Priority Data

Oct. 12, 1987 [GB] United Kingdom ............... 87 23931

[51] Int. Cl.⁵ ............................................ A61M 31/00
[52] U.S. Cl. .................................. 604/282; 604/175; 604/43; 604/29; 604/284
[58] Field of Search .................. 604/27, 28, 29, 39, 604/43, 94, 150, 175, 264, 275, 280, 283, 284, 282

[56] References Cited

U.S. PATENT DOCUMENTS

| | | | |
|---|---|---|---|
| 3,593,713 | 7/1971 | Bogoff | 128/246 |
| 4,184,497 | 1/1980 | Kolff et al. | 604/282 X |
| 4,392,855 | 7/1983 | Oreopoulus | 604/175 |
| 4,808,163 | 2/1989 | Laub | 604/105 |
| 4,841,976 | 6/1989 | Packard et al. | 128/657 |
| 4,861,333 | 8/1989 | Meador | 604/35 |

Primary Examiner—John D. Yasko
Assistant Examiner—Adams J. Cermak
Attorney, Agent, or Firm—Banner, Birch, McKie & Beckett

[57] ABSTRACT

A double lumen flexible catheter for peritonetal dialysis comprises a double lumen structure with inner and outer tubes. The outer tube has a plurality of openings the inner tube being stretched in tension to prevent kinking of the catheter. The inner tube has a single outlet at the free end of the catheter. The tubing for the catheter is sufficiently flexible to permit the catheter to lie loosely and freely in the body cavity. Treatment fluids are delivered to the peritoneal cavity through the inner tube and removed via the outer tube.

8 Claims, 1 Drawing Sheet

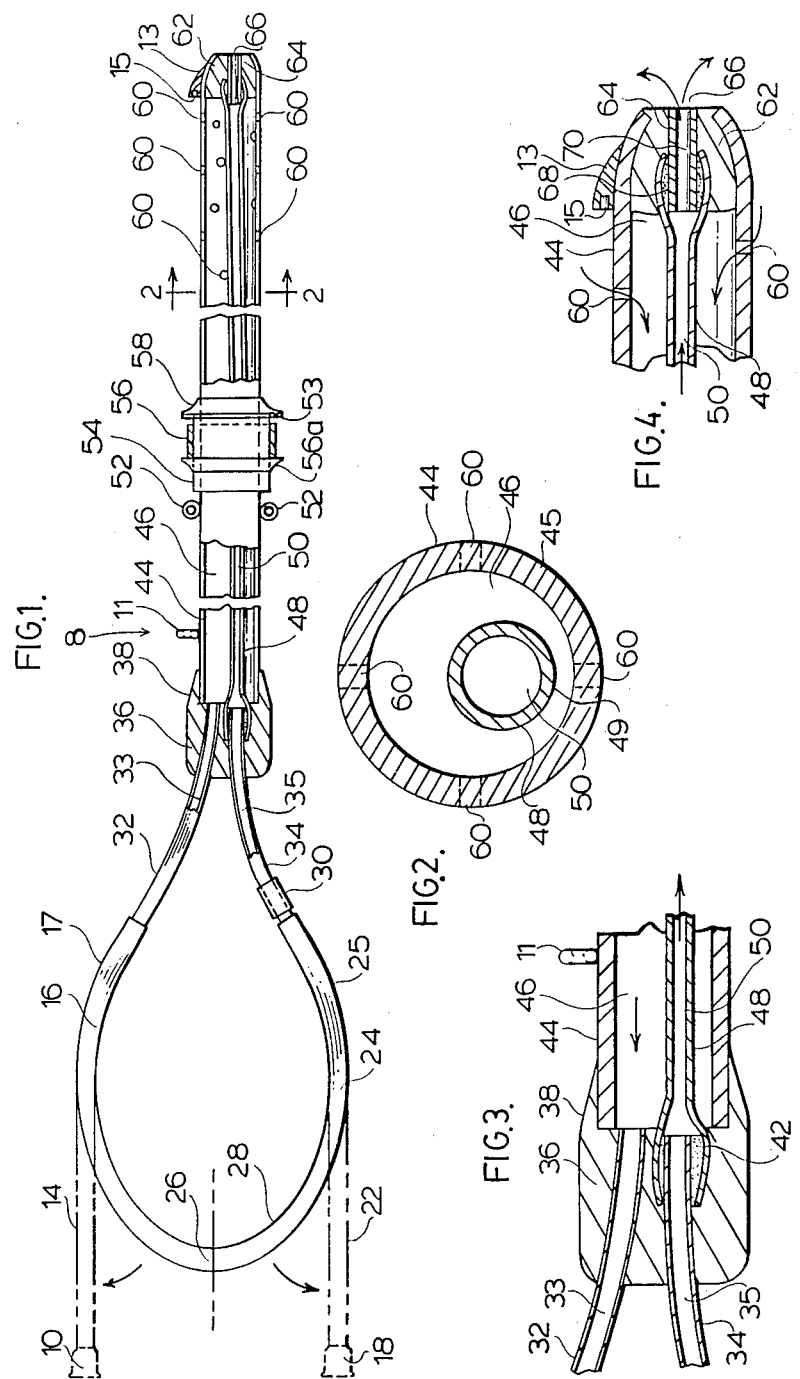

PERITONEAL DIALYSIS CATHETER SUITABLE FOR PERMANENT IMPLANT

FIELD OF THE INVENTION

This invention relates to a permanent catheter for use in the practice of peritoneal dialysis.

BACKGROUND OF THE INVENTION

In the practice of peritoneal dialysis, a dialysate is admitted to the peritoneal cavity of the patient through either a permanently implanted peritoneal catheter or more commonly through the use of a stab catheter. Such catheters have a perforated peritoneum section which lies within the peritoneal cavity. The catheter then extends exterior to the patient's body permitting the introduction of the dialysate from an external source.

The need for efficient peritoneal dialysis may be required either as a chronic medical treatment or in response to an acute medical episode. Renal failure is a common cause giving rise to the need for medical intervention through the use of peritoneal dialysis.

Peritoneal dialysis is often the preferred route of dialysis offering significant advantages over hemodialysis. While it is accepted that hemodialysis is more efficient than peritoneal dialysis, in the critically ill patient, peritoneal dialysis is often preferred because it allows for smoother fluid toxin and solute removal than hemodialysis. This may be necessary because of the patient's cardiovascular instability. Hemodialysis is not universally available. Many smaller hospitals do not have the necessary equipment to perform hemodialysis and therefore peritoneal dialysis would be the treatment of choice. Hemodialysis is very costly since expensive machines must be purchased and a nurse is required to be present for the duration of the procedure. This is not so for peritoneal dialysis, especially with the use of permanent catheter implantation. The increased convenience and decreased costs associated with peritoneal dialysis are significant advantages. Hemodialysis also requires a vascular access route into the patient which may not be available in some instances.

Efficient peritoneal dialysis is critical to patient care. Hypertonic dialysis fluid is instilled in the peritoneal cavity. Toxins in the bloodstream will diffuse through the peritoneal membrane along a concentration gradient into the peritoneal cavity, and water flows in similar direction along an osmotic gradient. As these toxins and other waste byproducts accumulate in the peritoneum, the concentration differentials decrease and the rate at which the toxins are removed from the bloodstream is reduced. Also, as glucose enters the blood stream from the dialysis fluid, the osmotic gradient for fluid removal diminishes with time. Continuous replacement of dialysis fluid in the peritoneal cavity will maintain these gradients providing optimal fluid and solute removal. Therefore to achieve efficient dialysis, the maintenance of a substantial concentration differential and the osmotic gradient between the blood vessels and the peritoneal cavity is essential.

At the present time, there are other catheters available which function as permanently implanted peritoneal dialysis devices. However, these devices are limited as to the maximum efficiency which can be achieved by the fact that they are single lumen devices. Reference would be drawn to U.S. Pat. No. 4,392,855.

There are dual lumen catheters in the marketplace which serve other purposes. For example, a number of patented devices can be found for hemodialysis and continuous blood sampling: U.S. Pat. Nos. 4,493,696; 4,583,968; 4,405,313; 4,626,240 and 4,601,697. Other dual lumen devices exist in the marketplace including devices of more general application (U.S. Pat. No. 701,075), devices for drainage of surgical fields (U.S. Pat. No. 3,528,427) and devices for intestinal intubation (U.S. Pat. No. 2,614,563).

The cited dual lumen hemodialysis patents can be differentiated from the present invention on the basis that they have been devised to address the unique problems arising in venous catherization, for example, ensuring ease of entry into the vein so as to prevent any kinking or buckling. To overcome this difficulty, venous catheters have been inventively adapted with smooth bore, semi-flexible, semi-rigid tips. This modification (seen in U.S. Pat. Nos. 4,493,696; 4,626,240; 4,583,968) permits the catheter to gently bend so as to yield to the shape of the vein yet retain sufficient rigidity so that the risk of kinking or buckling is minimized. A similar result is achieved in U.S. Pat. No. 4,405,313 by "filling-in" the area around the two tubes at the distal end of the catheter.

At present, all known peritoneal dialysis catheters, but one, have only a single lumen (U.S. Pat. No. 4,392,855; Tenckhoff and Schechter "A Bacteriologically Safe Peritoneal Access Device", *Trans. Amer. Soc. Artif. Int. Organs*, Vol XIV, 1968, pp 181-187). The Buyer's abdominal drainage tube, (U.S. Pat. No. 2,930,378) does exhibit a dual lumen structure, but it is distinguishable from the present invention in that both the inner tube and outer tube are perforated. The Buyer's device is suitable merely for drainage and could not function as a dual lumen dialysis device. The mixing of fluids between the inner and outer tubes would make it impossible to achieve the continuous flow dialysis envisioned by the present inventor. Furthermore, the overall structure of the Buyer's abdominal drainage tube would impede, if not render impossible, the necessary subcutaneous tunnelling required for permanent implantation.

The one remaining peritoneal dialysis catheter, which does have a double lumen structure similar to that of the applicant, is that of Nakamura, T. et al, "Continuous Peritoneal Dialysis with a Double Lumen Catheter for Acute Renal Failure in a New Born after Cardiac Surgery", *Japanese Journal of Intensive Care Medicine*, Vol 7, page 837, 1983 The Japanese peritoneal catheter is a straight, rigid device designed as a "stab" catheter.

SUMMARY OF THE INVENTION

According to an aspect of the invention, a double lumen flexible catheter is adapted for use in peritoneal dialysis by placement in a peritoneal cavity through an incision in body tissue defining the cavity. The catheter comprises:

a double lumen structure having a free distal end, means positioned above the distal end for connecting the double lumen structure to body tissue defining a peritoneal cavity and means proximal to the tissue connecting means for delivering fluids to and from the double lumen structure;

the double lumen structure comprising an inner tube and an outer tube with an annulus between them, the outer tube having a plurality of openings extending through its tube wall to permit cavity fluids to flow into the annulus, the inner tube having a single outlet at the catheter free end for delivering fluids into a body cavity;

the inner tube and outer tube being each of a plastics material of sufficient flexibility to permit the catheter to lie loosely and freely in a body cavity;

first means for anchoring the inner tube at the distal catheter free end and second means for anchoring the inner tube at the proximal fluid delivery end, the inner tube being stretched between the first and second anchoring means to apply tension on the outer tube between the first and second anchor means, the extent of tension in the inner tube is such to avoid drawing back the catheter free end to cause distortion in the catheter.

BRIEF DESCRIPTION OF THE DRAWINGS

Other and further advantages and features of the invention will be apparent to those skilled in the art from the following detailed description thereof, taken in conjunction with the accompanying drawings in which:

FIG. 1 presents an overall view of the proposed catheter, partially sectioned along the length of the catheter so as to reveal the positioning of the inner tube within the outer tube;

FIG. 2 is an enlarged cross-sectional view of the inner and outer tubes across the line 2—2 and illustrating the presence of perforations in the outer tube;

FIG. 3 is an enlarged longitudinal section through the Y-shaped proximal head of the catheter illustrating the points of attachment between the aseptic inflow and outflow tubes and the inner and outer tubes and illustrating the direction of fluid flows through this region;

FIG. 4 is an enlarged longitudinal section through the distal tip of the catheter illustrating the distal point of attachment of the stretched inner tube, the terminal obstruction of the outer lumen and illustrating the direction of fluid flows through this region.

DETAILED DESCRIPTION OF THE PREFERRED EMBODIMENTS

The peritoneal catheter, as illustrated in FIG. 1, is preferably constructed of a pliable medical grade silicon rubber (or similar flexible soft plastic equivalent), such as Silastic (trade mark) silicone rubber supplied by Dow Corning which has a durometer rating of fifty and having the necessary degree of flexibility so as to lie loosely and freely within the peritoneal cavity. The length of the outer tubing should be such that the distal, perforated portion of the cannula lies comfortably within the peritoneal cavity, whilst permitting that portion of the catheter extending proximally beyond the Dacron (trade mark) cuff to be tunneled through the subcutaneous tissues and to extend beyond the exterior of the patient's body. Distal and proximal are terms used in relation to that part of the surrounding outer tube which acts as a means for connection to the body tissues. Any part of the catheter which leads towards the body cavity is distal to this reference point, and any part of the catheter leading out of the body is proximal to this reference point. Throughout the detailed description of the preferred embodiments, the terms proximal and distal are intended to have this meaning. Therefore the proximal end of the catheter would be at the external loop 28 and the distal end of the catheter is at the end of the catheter having perforation 60. A surrounding hard plastic sleeve acts as the means for attachment to the body tissue. The device has on each side of the sleeve a lower and upper flange portion as well as a Dacron (trade mark) cuff between the two flanges and surrounding sleeve. The cuff and flanges said in holding the catheter in position and reducing the risk of inflammation and infection. This hard plastic attachment fits, as a sleeve, around the catheter. The lower flange portion of this hard plastic sleeve lies adjacent to the peritoneal membrane on the internal side of the peritoneal cavity. The hard plastic sleeve then extends through the peritoneal membrane and into a layer of muscle above the peritoneal membrane. The Dacron cuff surrounding the hard plastic sleeve extends through the muscular tissues above the peritoneal membrane. A pair of looped grommets are attached to the catheter just above the upper flange and these grommets extend into the subcutaneous tissues lying above the muscular tissues. These grommets can then be used to fix the catheter to these tissues. Beyond the looped grommets, the proximal section of the catheter is tunneled through the subcutaneous tissues and then exits through the patient's skin leaving the most proximal end of the catheter lying outside of the patient's body. The tunneling process is facilitated by the aseptic loop located at the most proximal end of the catheter. It is known that these tissue layers will integrate with the Dacron felted cuff to form scar tissue, effectively sealing the catheter in place. The hard plastic sleeve with flanges, Dacron and the proximal grommets facilitate the healing of the incision and a tight seal is formed around the catheter. The innovative grommets provide a point of attachment for a surgeon's sutures thereby further stabilizing the cannula at this critical juncture.

Stabilization of the catheter at its points of entry into and exit from the muscular and subcutaneous tissues is critical to maintaining the sterility of the peritoneum. Any catheter extending from the exterior portion of the patient's body to the interior provides a route of infection along which harmful bacteria and other microbiological organisms can travel from the asterile external environment, into the patient, and thereby cause infections. Peritoneal infections can put the patient at great risk and any innovation which minimizes this risk must be considered advantageous.

In addition, the preferred embodiment of the invention has an inner tube which has been stretched and thereby lies within the outer tube under tension. The stretched inner tube lies and moves freely within the lumen of the outer tube. Preferably the wall of the outer tube is substantially thicker than the wall of the inner tube. This extra thickness of the outer wall gives the catheter strength and durability. The extra thickness of the outer wall helps to reduce the possibility of the tube kinking or buckling. The provision of a stretched inner tube is a significant feature in the device of the present invention. Bending, kinking and buckling of catheters can be an undesirable consequence of designing a catheter of such flexible materials. A pliable catheter is definitely the preferred embodiment for an indwelling peritoneal catheter; therefore any innovation which minimizes risk of obstruction of the fluid flow by bending, kinking or buckling would be an important advantage. The tension created by stretching the inner tube within the outer tube acts to reduce this risk of obstruction by creating a force which will countervail, to a certain degree, the downward force created by the bend thereby permitting the fluid to flow through the bend. Tensioning of the central tube permits movement of the tube and allows it to flex with minimal occlusion, if any, when the tube is bent. To achieve the stretching both the proximal and distal ends of the inner tube are firmly anchored whilst still permitting fluid to flow freely from the entry point, throughout the length of the inner tube and into the peritoneum.

It is appreciated, however, that in some situations it is necessary, during insertion of the catheter into the cavity, to temporarily stiffen the catheter. According to this invention, the stiffening can be achieved by providing a releasable wire or the like on the catheter which is released from the catheter once it is properly positioned in the cavity.

The importance of this innovation is augmented when one considers that a freely floating pliable catheter, such as the instant invention, will naturally have a tendency to curve within the peritoneal cavity in the absence of a device fixing the location of the cannula.

The Oreopolous single lumen device (U.S. Pat. No. 4,392,855) suggests fixing the location of the cannula through the use of "flexible locating discs". These discs create certain difficulties such that the preferred embodiment of the applicant's peritoneal catheter would not include these locating discs. Experience has demonstrated that these discs interfere with the removal of the peritoneal catheter when the patient no longer requires the catheter. Also, during the period of time that the catheter is implanted, said discs may cause discomfort and even pain to the patient. For these reasons, a freely floating cannula would be one aspect of the preferred embodiment of this invention. The innovative stretching of the inner tube would minimize the risk of obstruction by bending of the cannula while laying in the peritoneum.

The inner tube is stretched only to a limiting point and no further. Beyond this point, there would be a tendency to draw back the distal portion of the catheter upon itself, i.e., the tension in the inner tube as applied to the outer tube does not distort the elongate shape of the catheter.

In addition, the preferred embodiment of the invention has firmly bonded points of attachment or anchoring at the proximal and distal ends of the stretched inner tube which have been devised so as not to impede the fluid flow. Such bonding is preferably achieved through the use of Silastic medical adhesive type A (referred to herein as "medical grade glue") manufactured by Dow Corning, or any other suitable medical grade bonding adhesive. The distal point of attachment is devised so that the inner lumen extends beyond the outer lumen, the outer lumen being plugged with a strong bond of medical grade glue so as to prevent mixing of the inflow and outflow fluids. To further reduce the possibility of mixing, the perforations in the distal portion of the cannula do not extend within approximately 0.5 cm of the distal tip of the catheter. Any reduction in mixing would be advantageous, since decreased mixing will increase the solute concentration differential.

To maintain sterility throughout the interior luminal regions of the catheter, the inflow and outflow tubes have been interconnected so as to form a closed, aseptic environment thereby significantly reducing the opportunity for intraluminal contamination during surgical implantation. Said aseptic loop forms part of the preferred embodiment of this invention. This innovative aseptic loop also performs a second useful function to facilitate tunnelling through the subcutaneous tissues during implantation, whereby the loop can be grasped by the surgeon's forceps and thereby pulling the proximal portion of the catheter through the subcutaneous tissues and out to the exterior of the patient's body without contaminating the interior lumens of the catheter. After the catheter has been implanted in the patient, then the loop can be cut in its intermediate portion and connected to the appropriate equipment regulating the inflow and outflow of fluids through the inner and outer tubes respectively.

Referring now to the drawings, a catheter 8, according to the present invention, includes a silicon rubber, tubular, outer tube 44 with a silicon rubber, tubular, inner tube 48 fully contained within the lumen 46 of the outer tube 44. As shown in FIG. 2, the inner tube 48 has a cross-sectional diameter which is substantially less than that of the outer tube 44, the inner tube 48 being fully contained within the outer tube 44 and able to move freely within the outer lumen 46. Also shown in FIG. 2, the thickness 45 of the wall of the outer tube 44 is greater than the thickness 49 of the inner tube 48.

As shown in FIG. 3, the proximal end of the inner tube 48 is stretched over the distal end of a silicon rubber inflow connector tube 34 being attached one to the other by a medical grade glue 42. Both the inner tube 48 and the inflow connector tube 34 are glued 36 using medical grade glue, to an external silicon rubber cuff 38 which serves to hold all of the connecting tubes in position as well as forming a stabilization point for the inflow tube 25 and the outflow tube 17 which extend beyond the cuff stabilization point 38. Lumen 50 of the inner tube 48 and lumen 35 of the inflow connector tube 34 are continuous and unobstructed.

As shown in FIG. 3, the distal end of a silicon rubber outflow connector tube 32 is inserted into the proximal end of the outer tube 44 and attached thereto by means of a medical grade glue 36. The lumen 33 of the outflow connector tube 32 and the lumen 46 of the outer tube 44 are continuous and unobstructed. Both the outflow connector tube 32 and the inflow connector tube 34, and the outer tube 44 are glued, using medical grade glue 36, to the inside of the external silicon rubber cuff 38.

FIG. 4 shows the inner tube 48 connected at its distal end to a silicon rubber connector tube 64 by means of stretching the distal end of the inner tube 48 over top of the proximal end of the connector tube 64 such that the inner lumen 50 is continuous with the inner lumen 70 providing a continuous pathway for fluid flow of the dialysate through the distal tip 66 of catheter 8 into the peritoneal cavity. The distal end of the inner tube 48 is attached to the connector tube 64 by means of a medical grade glue 68. Connector tube 64 may be radiopaque. The distal connector tube 64 is centrally located with the outer tube 44 being centrally fixed by the use of a medical grade glue 62. Said medical grade glue 62 also serves to tightly seal off the outer lumen 46, thereby reducing the possibility for any mixing of the inflowing and outflowing fluids.

FIGS. 1 and 2 show a plurality of perforations 60 in the distal portion of the cannula. These perforations begin no less than 0.5 cm away from the bottom of flange 58 and preferably more than 1.5 cm. The perforations extend distally around the outer tube 44 perforating the outer tube 44 completely so as to provide an unobstructed pathway for flow of the peritoneal fluids into the outer lumen 46. The perforations 60 extend to a point no closer than 0.5 cm from the distal tip 66 of catheter 8. The pathway of outward flowing dialysate from the distal tip 66 and the inward flowing peritoneal fluids through the perforations 60 is illustrated in FIG.

4. The perforations generally range between 0.1 mm and 3.0 mm in diameter and preferably 0.5 mm to 3.0 mm and can cover any portion of the distal section of the outer tube 44 as desired within the limits described above.

At the junction between the proximal portion of the catheter 8 extending into the subcutaneous tissue and exterior to the patient and the distal portion of the catheter 8 lying in the peritoneal cavity is a hard plastic sleeve 54 which fits snugly over the outer tube 44 and is fixed at a location roughly halfway down the length of the outer tube 44. The distal portion of the hard plastic sleeve is defined by two circular flanges 58 and 56a which completely encompasses the circumference of the outer tube 44. The distal flange 58 lies flat against the inner peritoneal membrane, within the peritoneal cavity, providing a barrier to entry by infectious agents into the peritoneum. The proximal flange 56a lies against the outer surface of the peritoneal membrane, and prevents the proximal portion of the catheter from sliding into the peritoneal cavity. A Dacron felt cuff sleeve envelopes the hard plastic sleeve proximal to the proximal flange and distal to the looped silicon rubber grommets. A portion 53 of the hard plastic sleeve 54 then extends through the incision in the peritoneal membrane into the muscular tissues with the Dacron felt cuff 54 thereby resting in the muscular layer near the subcutaneous side of the abdomen enabling the tissues to attach by way of cellular ingrowth to the Dacron felt cuff 56 and form a fibrous seal providing a further barrier to entry by infection agents into the peritoneal cavity. Located at the top of the hard plastic seal 56 are a pair of circular grommets 52 which extend away from the outer tube 44 and provide a further point of attachment to the subcutaneous tissues thereby stabilizing and fixing the catheter and thereby providing a firm seal between the interior and exterior aspects of the peritoneum.

That section of the cannula extending proximally beyond the hard plastic sleeve 54 is surgically tunnelled through the subcutaneous tissues for a short distance and then extruded through an incision in the skin into an area which is external to the patient's body. The aseptic proximal loop 28 provides a means by which the surgeon can grasp hold of the catheter 8 and pull the catheter 8 through the subcutaneous tissues and out beyond the patient's body without contaminating the intraluminal regions 24, 16, 35, 33, 46 and 50 and facilitating the tunneling process.

The proximal loop 28 lies entirely outside of the patient's body. The distal end of the inflow arm 25 of loop 28 stretches over the proximal end of the inflow connector tube 34 and the two are adhesively attached with a medical grade glue such that the lumen 24 of the inflow arm 25 and the lumen 35 of the inflow connector tube 34 are continuous and unobstructed. Similarly, the distal end of the outflow arm 17 of loop 28 stretches over the proximal end of the outflow connector tube 32 such that the lumen 16 of the outflow arm 17 and the lumen 33 of the outflow connector tube 32 are continuous and unobstructed.

The inflow arm 25 and the outflow arm 17 are in fact opposite ends of a common tube. This common tube forms the aseptic loop 28. Once the catheter has been implanted in the patient, the aseptic loop 28 can be cut, at cut point 26, using common sterile technique, creating two distinct inflow and outflow tubes 22 and 14 respectively. The open ends are then available to be fitted with the appropriate inflow adapter 18 and outflow adapter 10. In most situations, it will not be necessary to stiffen the catheter for insertion into the cavity. However, if stiffening is required, the following technique is preferred. A stainless steel wire is feed through eye 11 at the proximal end of the catheter. The distal end of the wire, as fed through eye 11, is inserted in holder 13 having an opening 15. The wire may be curved or bent to facilitate and direct catheter insertion. Once the catheter is positioned in the cavity, the wire is removed so that the catheter is free to flex as needed with the cavity.

A marker 30 is located on the inflow connector tube 34 indicating this to be the tube through which the dialysate flows into the catheter device.

A continuous inflow pathway of the dialysate fluids extends through the inflow adaptor 18 into lumen 24 of the inflow tube 22 into lumen 35 of the inflow connector tube 34 into lumen 50 of the inner tube 48 and into lumen 70 of the distal connector tube 64. Similarly, a continuous outflow pathway of the peritoneal fluids extends through the perforations 60 into lumen 46 of the outer tube 44 into lumen 33 of the outflow connector tube 32 into lumen 16 of the outflow tube 14 and through the outflow adaptor 10.

The invention illustrated and described herein in detail need not be limited only to insertion into peritoneal cavities. It is understood that such a double lumen catheter device could function effectively if placed in any body cavity of suitable size where continuous flushing and drainage were required. In the same way that the length of the catheter could be lengthened or shortened so as to adjust to the size of the patient's peritoneum, ranging from infants to adults, so too it could be modified to adjust to variously sized body cavities.

While the presently envisioned immediate use for such a device is for treatment of acute renal failure, it is understood that this device could also be used effectively in cases of chronic renal failure. As well, it is appreciated that the described invention could also be used to treat cases of poisonings and severe metabolic derangements. Such a device could be implanted during surgery and used as a means of flushing the appropriate cavity with antibiotics or antiseptic solutions until the healing process is sufficiently under way at which time the device would be removed.

The dual lumen system provided by this invention is expected to maintain a greater solute concentration and osmotic gradient over that of a similar single lumen device and therefore achieve greater dialysis efficiency. As well, the dual lumen system permits continuous flushing whereas the single lumen devices lie passively in the peritoneal cavity allowing fibrin to collect on the device possibly leading to obstruction of the single lumen flow pathway. It is understood that the continuous flushing, which is possible by use of the applicant's invention, should inhibit such fibrin accumulation thereby reducing the risk of blockage of the perforations and tubal lumens.

The rigidity of "stab catheters" renders permanent implantation impossible. Experience has shown that their use is generally limited to a few days and thereafter the patient would then have to be "stabbed" (re-catheterized) again. Considering that continuous dialysis for as long as several weeks is often the recommended method of treatment for the acutely ill patient, the impracticalities of the rigid, stab method of catherization become readily apparent.

The two key routes by which peritoneal infection can arise are via the lumen of the dialysis catheter (transluminally) and along the outside of the dialysis catheter. The risks of infection and inflammation with these repeated catheter "stabs" are substantially greater than with the use of permanently implanted peritoneal catheters. With rigid catheters, the opening through the skin down to the peritoneum will readily loosen around the catheter providing easy access for external infectious agents to enter the peritoneum substantially increasing the risk of infection and inflammation. The applicant's device incorporates methodologies and apparatus which serve to minimize transmission of external infections along the outside of the catheter into the peritoneum. Similarly, the applicant's aseptic loop provides a means for substantially minimizing the opportunities for transluminal transmission of external infectious agents into the peritoneum.

Peritoneal dialysis is often the preferred method of treatment over other means of dialysis such as hemodialysis, because of its significantly reduced cost, increased convenience, the opportunity for long term continuance dialysis and maintenance and the fact that it does not require vascular access.

Although preferred embodiments of the invention have been described herein in detail, it will be understood by those skilled in the art that variations may be made thereto without departing from the spirit of the invention or the scope of the appended claims.

We claim:

1. A double lumen flexible catheter adapted for use in peritoneal dialysis by placement in a peritoneal cavity through an incision in body tissue defining a peritoneal cavity, said catheter comprising:

a double lumen structure having means for connecting said double lumen structure to body tissue defining a peritoneal cavity, a free end distal to said tissue connecting means, and means proximal to said tissue connecting means for delivering fluids to and from said double lumen structure;

said double lumen structure comprising an inner tube and an outer tube with an annulus between them, said outer tube having a plurality of openings extending through its tube wall to permit cavity fluids to flow into said annulus, said inner tube having a single outlet at said catheter free end for delivering fluids into a body cavity;

said inner tube and outer tube being each of a plastic material of sufficient feasibility to permit said catheter to lie loosely and freely in a body cavity;

first means for anchoring said inner tube at said distal catheter free end and second means for anchoring said inner tube at said proximal fluid delivery end, said inner tube being stretched between said first and second anchoring means to apply tension on said inner tube between said first and second anchor means, the extent of tension in said inner tube is such to avoid drawing back said catheter free end to cause distortion in said catheter.

2. A catheter of claim 1 wherein said outer tube has a wall thickness greater than the wall thickness of said inner tube.

3. A catheter of claim 1 wherein both said anchor means comprise a biocompatible adhesive for plastics of said inner and outer tubes.

4. A catheter of claim 1 wherein said catheter free end is radiopaque.

5. A catheter of claim 1 wherein said openings in said outer tube are each approximately 0.5 to 1.0 mm in diameter.

6. A catheter of claim 1 wherein said outlet of said inner tube is spaced at least 0.5 cm from the closest one of said openings in said outer tube.

7. A catheter of claim 1 wherein said means surrounding said outer tube for connection to body tissue includes a pair of hooped grommets as suture attachment points thereby facilitating the immobilization of the catheter in said body tissue.

8. A catheter of claim 1 wherein a length of tubing interconnects said inner and outer tubes at their respective proximal ends, said length of tubing being sterile and thereby maintaining sterility within said inner and outer tubes during implantation of said catheter in a body cavity after said implantation, said length of tubing being severable at its intermediate portion thereby permitting attachment of said inner and outer tubes to the appropriate inflow and outflow regulatory equipment.

* * * * *